United States Patent
Reh et al.

(10) Patent No.: US 7,541,186 B2
(45) Date of Patent: Jun. 2, 2009

(54) METHOD OF GENERATING HUMAN RETINAL PROGENITORS FROM EMBRYONIC STEM CELLS

(75) Inventors: Thomas Reh, Seattle, WA (US); Deepak Lamba, Seattle, WA (US)

(73) Assignee: University of Washington, Seattle, WA (US)

( * ) Notice: Subject to any disclaimer, the term of this patent is extended or adjusted under 35 U.S.C. 154(b) by 341 days.

(21) Appl. No.: 11/361,051

(22) Filed: Feb. 22, 2006

(65) Prior Publication Data

US 2007/0196919 A1 Aug. 23, 2007

(51) Int. Cl.
*C12N 5/00* (2006.01)

(52) U.S. Cl. .................. 435/377; 435/325; 435/375
(58) Field of Classification Search .................. None
See application file for complete search history.

(56) References Cited

U.S. PATENT DOCUMENTS 5,453,357 A * 9/1995 Hogan .................. 435/7.21

FOREIGN PATENT DOCUMENTS

| WO | WO 00/20599 | 4/2000 |
|---|---|---|
| WO | WO 02/076386 A2 | 10/2002 |
| WO | WO 2004/007749 A2 | 1/2004 |

OTHER PUBLICATIONS

Hoepfl G et al. 2004. "Differentiating embryonic stem cells into embryoid bodies." in Schatten H, ed. Methods in Molecular Biology 254: 79-80.*
Lamba Da et al. 2006. Efficient genereation of retinal progenitor cells from human embryonic stem cells. Proc Natl Acad Sci USA 103: 12769-12774.*
Anchan, R. et al., "EGF and TGF-α stimulate retinal neuroepithelial cell proliferation in vitro," (1991) *Neuron*, 6:923-936.
Coles, B., et al., "Facile isolation and the characterization of human retinal stem cells," (2004) *PNAS*, 101(44):15772-15777.
Ikeda, H., et al., "Generation of Rx+/Pax6+ neural retinal precursors from embryonic stem cells," (2005) *PNAS*, 102(32):11331-11336.
Kelley, M., et al., "Retinoic acid promotes differentiation of photoreceptors in vitro," (1994) *Development*, 120:2091-2102.
Kelley, M., et al., "Regulation of proliferation and photoreceptor differentiation in fetal human retinal cell cultures," (1995) *investigative Opthamology &Visual Science*, 36(7):1280-1289.
Kelley, M., et al., "Ligands of steroid/thyroid receptors induce cone photoreceptors in vertebrate retina," (1995) *Development*, 121:3777-3785.
Klassen, H., et al., "Stem cells and retinal repair," (2004) *Progress in Retinal and Eye Research*, 23:149-181.
Meyer, J., et al., "Embryonic stem cell-derived neural progenitors incorporate into degenerating retina and enhance survival of hose photoreceptors," (2005) *Stem Cells Express*, published online, doi:10.1634/stemcells.2005-0059.
Ornitz, D., et al., "Receptor specificity of the fibroblast growth factor family," (1996) *The Journal of Biological Chemistry*, 271(25):15292-15297.
Reh, T. and Levine, E., "Multipotential stem cells and progenitors in the vertebrate retina," (1998) *Department of Biological Structure*, University of Washington, 206-220.
Taylor, M., and Reh, T., "Induction of differentiation of rat retinal, germinal, neuroepithelial cells by dbcAMP," (1990) *Journal of Neurobiology*, 21(3):470-481.
Yang, P., et al., "In vitro isolation and expansion of human retinal progenitor cells," (2002) *Experimental Neurology*, 177:326-331.
Zaghloul, N., et al., "Step-wise specification of retinal stem cells during normal embryogenesis," (2005) *Biology of the Cell*, 97(5):321-337.

* cited by examiner

*Primary Examiner*—Lora E Barnhart
(74) *Attorney, Agent, or Firm*—Bozicevic, Field & Francis LLP; Pamela J. Sherwood

(57) ABSTRACT

Methods are provided for the in vitro differentiation of human retinal progenitor cells from embryonic stem cells.

8 Claims, 7 Drawing Sheets

| Gene | Primer Pairs |
|---|---|
| β-actin | F-actcttccagccttccttc R-atctccttctgcatcctgtc |
| Otx-2 | F-gcagaggtcctatcccatga R-ctgggtggaaagagaagctg |
| Emx-1 | F-aggtgaaggtgtggttccag R-agtcattggaggtgacatcg |
| Pax-6 | F-tctaatcgaagggccaaatg R-tgtgagggctgtgtctgttc |
| Lhx-2 | F-tagcatctactgcaaggaagac R-gtgataaaccaagtcccgag |
| Six-3 | F-ggaatgtgatgtatgatagcc R-tgatttcggtttgttctgg |
| Rx | F-gaatctcgaaatctcagccc R-cttcactaatttgctcaggac |
| C-Myb | F-tacccaactgttcacgcaga R-ctttccacaggatgcaggtt |
| Neurogenin-2 | F-ctcttctccgaggcagtgtt R-ggctgccaatagtccatgtc |
| Hash-1 | F-cggccaacaagaagatgagt R-gccatggagttcaagtcgtt |
| Crx | F-atgatggcgtatatgaaccc R-tcttgaaccaaacctgaacc |
| Rhodopsin | F-tcatcatggtcatcgctttc R-catgaagatgggaccgaagt |
| S-Opsin | F-gatgaatccgacacatgcag R-ctgttgcaaacaggccaata |
| Recoverin | F-ccagagcatctacgccaagt R-cacgtcgtagagggagaagg |
| PDE-β | F-aggagaccctgaacatctacc R-atgaagcccacttgcagc |
| Engrailed-1 | F-ccgcaccaccaactttttcat R-tggacagggtctctacctgc |
| Math-5 | F-ccgaacaggacaaactcaca R-tcgcatcatcagacctatgg |

FIGURE 6

SEQUENCE LISTING

<160> NUMBER OF SEQ ID NOS: 34

<210> SEQ ID NO 1
<211> LENGTH: 19
<212> TYPE: DNA
<213> ORGANISM: H. sapiens

<400> SEQUENCE: 1
actcttccag ccttccttc                                                19

<210> SEQ ID NO 2
<211> LENGTH: 20
<212> TYPE: DNA
<213> ORGANISM: H. sapiens

<400> SEQUENCE: 2
atctccttct gcatcctgtc                                               20

<210> SEQ ID NO 3
<211> LENGTH: 20
<212> TYPE: DNA
<213> ORGANISM: H. sapiens

<400> SEQUENCE: 3
gcagaggtcc tatcccatga                                               20

<210> SEQ ID NO 4
<211> LENGTH: 20
<212> TYPE: DNA
<213> ORGANISM: H. sapiens

<400> SEQUENCE: 4
ctgggtggaa agagaagctg                                               20

<210> SEQ ID NO 5
<211> LENGTH: 20
<212> TYPE: DNA
<213> ORGANISM: H. sapiens

<400> SEQUENCE: 5
aggtgaaggt gtggttccag                                               20

<210> SEQ ID NO 6
<211> LENGTH: 20
<212> TYPE: DNA
<213> ORGANISM: H. sapiens

<400> SEQUENCE: 6
agtcattgga ggtgacatcg                                               20

<210> SEQ ID NO 7
<211> LENGTH: 20
<212> TYPE: DNA
<213> ORGANISM: H. sapiens

<400> SEQUENCE: 7
tctaatcgaa gggccaaatg                                               20

<210> SEQ ID NO 8
<211> LENGTH: 20
<212> TYPE: DNA
<213> ORGANISM: H. sapiens

<400> SEQUENCE: 8
tgtgagggct gtgtctgttc						20

<210> SEQ ID NO 9
<211> LENGTH: 22
<212> TYPE: DNA
<213> ORGANISM: H. sapiens

<400> SEQUENCE: 9
tagcatctac tgcaaggaag ac					22

<210> SEQ ID NO 10
<211> LENGTH: 20
<212> TYPE: DNA
<213> ORGANISM: H. sapiens

<400> SEQUENCE: 10
gtgataaacc aagtcccgag						20

<210> SEQ ID NO 11
<211> LENGTH: 21
<212> TYPE: DNA
<213> ORGANISM: H. sapiens

<400> SEQUENCE: 11
ggaatgtgat gtatgatagc c						21

<210> SEQ ID NO 12
<211> LENGTH: 19
<212> TYPE: DNA
<213> ORGANISM: H. sapiens

<400> SEQUENCE: 12
tgatttcggt ttgttctgg						19

<210> SEQ ID NO 13
<211> LENGTH: 20
<212> TYPE: DNA
<213> ORGANISM: H. sapiens

<400> SEQUENCE: 13
gaatctcgaa atctcagccc						20

<210> SEQ ID NO 14
<211> LENGTH: 21
<212> TYPE: DNA
<213> ORGANISM: H. sapiens

<400> SEQUENCE: 14
cttcactaat ttgctcagga c						21

<210> SEQ ID NO 15
<211> LENGTH: 20
<212> TYPE: DNA
<213> ORGANISM: H. sapiens

<400> SEQUENCE: 15
tacccaactg ttcacgcaga						20

<210> SEQ ID NO 16
<211> LENGTH: 20
<212> TYPE: DNA

<213> ORGANISM: H. sapiens

<400> SEQUENCE: 16
ctttccacag gatgcaggtt                                               20

<210> SEQ ID NO 17
<211> LENGTH: 20
<212> TYPE: DNA
<213> ORGANISM: H. sapiens

<400> SEQUENCE: 17
ctcttctccg aggcagtgtt                                               20

<210> SEQ ID NO 18
<211> LENGTH: 20
<212> TYPE: DNA
<213> ORGANISM: H. sapiens

<400> SEQUENCE: 18
ggctgccaat agtccatgtc                                               20

<210> SEQ ID NO 19
<211> LENGTH: 20
<212> TYPE: DNA
<213> ORGANISM: H. sapiens

<400> SEQUENCE: 19
cggccaacaa gaagatgagt                                               20

<210> SEQ ID NO 20
<211> LENGTH: 20
<212> TYPE: DNA
<213> ORGANISM: H. sapiens

<400> SEQUENCE: 20
gccatggagt tcaagtcgtt                                               20

<210> SEQ ID NO 21
<211> LENGTH: 20
<212> TYPE: DNA
<213> ORGANISM: H. sapiens

<400> SEQUENCE: 21
atgatggcgt atatgaaccc                                               20

<210> SEQ ID NO 22
<211> LENGTH: 20
<212> TYPE: DNA
<213> ORGANISM: H. sapiens

<400> SEQUENCE: 22
tcttgaacca aacctgaacc                                               20

<210> SEQ ID NO 23
<211> LENGTH: 20
<212> TYPE: DNA
<213> ORGANISM: H. sapiens

<400> SEQUENCE: 23
tcatcatggt catcgctttc                                               20

<210> SEQ ID NO 24
<211> LENGTH: 20

-continued

<212> TYPE: DNA
<213> ORGANISM: H. sapiens

<400> SEQUENCE: 24
catgaagatg ggaccgaagt                                          20

<210> SEQ ID NO 25
<211> LENGTH: 20
<212> TYPE: DNA
<213> ORGANISM: H. sapiens

<400> SEQUENCE: 25
gatgaatccg acacatgcag                                          20

<210> SEQ ID NO 26
<211> LENGTH: 20
<212> TYPE: DNA
<213> ORGANISM: H. sapiens

<400> SEQUENCE: 26
ctgttgcaaa caggccaata                                          20

<210> SEQ ID NO 27
<211> LENGTH: 20
<212> TYPE: DNA
<213> ORGANISM: H. sapiens

<400> SEQUENCE: 27
ccagagcatc tacgccaagt                                          20

<210> SEQ ID NO 28
<211> LENGTH: 20
<212> TYPE: DNA
<213> ORGANISM: H. sapiens

<400> SEQUENCE: 28
cacgtcgtag agggagaagg                                          20

<210> SEQ ID NO 29
<211> LENGTH: 21
<212> TYPE: DNA
<213> ORGANISM: H. sapiens

<400> SEQUENCE: 29
aggagaccct gaacatctac c                                        21

<210> SEQ ID NO 30
<211> LENGTH: 18
<212> TYPE: DNA
<213> ORGANISM: H. sapiens

<400> SEQUENCE: 30
atgaagccca cttgcagc                                            18

<210> SEQ ID NO 31
<211> LENGTH: 21
<212> TYPE: DNA
<213> ORGANISM: H. sapiens

<400> SEQUENCE: 31
ccgcaccacc aactttttca t                                        21

<210> SEQ ID NO 32

```
<211> LENGTH: 20
<212> TYPE: DNA
<213> ORGANISM: H. sapiens

<400> SEQUENCE: 32
tggacagggt ctctacctgc                                               20

<210> SEQ ID NO 33
<211> LENGTH: 20
<212> TYPE: DNA
<213> ORGANISM: H. sapiens

<400> SEQUENCE: 33
ccgaacagga caaactcaca                                               20

<210> SEQ ID NO 34
<211> LENGTH: 20
<212> TYPE: DNA
<213> ORGANISM: H. sapiens

<400> SEQUENCE: 34
tcgcatcatc agacctatgg                                               20
```

METHOD OF GENERATING HUMAN RETINAL PROGENITORS FROM EMBRYONIC STEM CELLS

STATEMENT REGARDING FEDERALLY SPONSORED RESEARCH

This invention was made with government support under grant no. P20GM69983 awarded by the National Institute of Health. The government may have certain rights in this invention.

BACKGROUND OF THE INVENTION

Neuronal degeneration is the cause of debilitating visual impairment associated with prevalent ocular diseases, such as retinitis pigmentosa (RP), age-related macular degeneration (AMD), retinoschisis, lattic degeneration, retinal detachment, and glaucoma. Other causes of visual impairment include artery or vein occlusion and diabetic retinopathy. Current treatment of these diseases remains unsatisfactory.

The identification and characterization of neural and retinal progenitor cells has opened new pathways for treating diseases associated with neuronal degeneration. Progenitor cells may help to restore vision in patients who have these diseases, by repopulating the damaged retina and/or by rescuing retinal neurons from further degeneration. In cellular replacement therapies, retinal progenitor cells or differentiated progeny are transplanted to replace diseased tissue. Cell replacement therapy may replace damaged cells with cultured stem/progenitor cells, or with endogenous stem/progenitor cells. Alternatively, genetically engineered stem or progenitor cells can be used to target gene products to sites of degeneration. These gene products can include survival-promoting factors to rescue degenerating neurons, factors that can act in an autocrine manner to promote survival and differentiation of grafted cells into site-specific neurons or to deliver neurotransmitter(s) to permit functional recovery.

Progenitor cells of the neural retina have been described as giving rise to all the neurons, photoreceptors, and the Muller glia of the eye. These progenitor cells have a simple bipolar morphology, and in most cases undergo their mitotic divisions at the ventricular surface. Immediately after their final mitotic division, one or both of the daughter cells begin to express characteristics of differentiating neurons. In the early embryonic retina, many of the divisions of the progenitor cells are symmetric; both progeny of a particular division can remain progenitor cells and continue to divide, although some of the mitotic divisions are asymmetric, with a particular division yielding a neuron and another progenitor cell, or two neurons of different types.

The lineages of the various types of retinal neurons share a common progenitor. Progeny of a single cell have been shown to include many different types of retinal neurons, and some clones contain a combination of both retinal neurons and Muller glia, the intrinsic glial cell of the retina. Progenitor cells can give rise to a neuron and a glial cell, two glia, two of the same type of neurons, or two different types of neurons. Thus, there is no strict lineage relationships among the different types of retinal cells.

Retinal progenitor cells have been isolated from embryonic tissues and grown in culture (Reh and Kljavin, 1989). Such cultures typically include growth factors such as epidermal growth factor (EGF) and transforming growth factor-α (TGF-α). Peptides that stimulate receptor tyrosine kinases (e.g. FGF), serine threonine kinases (TGF-β3), and the hedgehog signaling pathway (Shh) can all influence the types of neurons that differentiate in the cultures. Thus, several different signaling systems are involved in the specification of cell identity and cell-specific gene expression. Many factors have opposing effects on the generation of the different retinal cell types; for example, TGF-α stimulates amacrine cell production but inhibits rod photoreceptor differentiation, while retinoic acid stimulates the progenitor to produce rods but prevents additional amacrine cells from differentiating in the culture. A large number of different types of factors, including extracellular matrix molecules such as S-laminin, and highly diffusible factors such as retinoic acid have been shown to affect photoreceptor differentiation, while fewer types of factors have been shown to have effects on the development of the other cell types.

The expansion of primary cultures of human retinal progenitors has potential for providing a source for transplantation to treat degenerative conditions of the retina such as macular degeneration and retinitis pigmentosa. However, it is difficult to obtain sufficient quantities of these cells from primary tissue. The ability to differentiate human retinal progenitors from stem cells would be of great interest for these purposes. The present invention addresses this issue.

REFERENCES

Kelley et al. (1995) Retinoid/thyoid receptor ligands regulate the ratios of rod and cone photoreceptors in developing retinal cell cultures. Development 121: 3777-3785; Levine et al. (1997) Sonic hedgehog promotes rod photoreceptor differentiation in mammalian retinal cell in vitro. J. Neuroscience 17: 6277-6288; Reh and Levine (1998) Multipotential Stem Cells and Progenitors in the Vertebrate Retina. J. Neurobiol. 6:206-220.

Kelley et al. (1994) Retinoic acid promotes differentiation of photoreceptors in vitro. Development 120(8):2091-102; Anchan et al. (1991) EGF and TGF-alpha stimulate retinal neuroepithelial cell proliferation in vitro. Neuron. 6(6):923-36; Taylor and Reh (1990) Induction of differentiation of rat retinal, germinal, neuroepithelial cells by dbcAMP. J Neurobiol. 21(3):470-81; Kelley et al. (1995) Regulation of proliferation and photoreceptor differentiation in fetal human retinal cell cultures. Invest Ophthalmol Vis Sci. 36(7):1280-9.

Yang et al. (2002) Exp. Neurology 177:26-1; Coles et al. (2004) PNAS 101:15772-15777.

Ikeda et al. (2005) PNAS 102:111-116; Meyer et al. (2005) Stem Cells.

SUMMARY OF THE INVENTION

Methods are provided for the in vitro differentiation of human embryonic stem cells to retinal progenitor cells, which are multipotent cells that can give rise to neurons, photoreceptors, and the Muller glia of the eye. The methods also include further differentiation of such retinal progenitor cells to differentiated progeny, e.g. neurons, photoreceptors and glia. The methods of the invention provide for substantially pure populations of retinal progenitor cells, where at least about 50% of the cells in the composition may be retinal progenitor cells, or differentiated progeny thereof. The cell populations thus obtained find use in screening assays; as a source of specific biomolecules associated with retinal differentiation; for therapeutic purposes such as treatment of neuronal degeneration of the eye; and the like.

Embryonic stem cells are cultured to differentiate into embryoid bodies in the presence of a cocktail of factors that direct differentiation to an anterior neural fate, which cocktail includes, without limitation, an antagonist of bone morphogenetic protein (BMP) signaling pathways; an antagonist of wnt signaling pathways; and an IGF1R agonist, in the absence of basic fibroblast growth factor (FGF2) activity. The resulting embryoid bodies are plated in medium comprising an antagonist of bone morphogenetic protein (BMP) signaling pathways; an antagonist of wnt signaling pathways; an IGF1R agonist; and a molecule that provides FGF2 activity, and are cultured for a period of time sufficient to allow retinal differentiation. The cells thus obtained may be used directly, or may be further isolated, e.g. in a negative selection to remove ES cells.

The methods of the invention provide means to study the mechanisms of retinal development; and a physiological system for drug screening to identify agents that act on retinal cells or that modulate the process of retinal development. Such methods involve combining a candidate agent with the cell population of the invention, and then determining any modulatory effect resulting from the compound. This may include examination of the cells for toxicity, metabolic change, or an effect on cell function.

These and other embodiments of the invention will be apparent from the description that follows. The compositions, methods, and techniques described in this disclosure hold considerable promise for use in diagnostic, drug screening, and therapeutic applications.

BRIEF DESCRIPTION OF THE DRAWINGS

FIG. 6. Quantitative RT-PCR primers. Gene Primer Pairs β-actin (SEQ ID NO:1) F-actcttccagccttccttc; (SEQ ID NO:2) R-atctccttctgcatcctgtc; Otx-2 (SEQ ID NO:3) F-gca-gaggtcctatcccatga; (SEQ ID NO:4) R-ctgggtggaaagagaagctg; Emx-1 (SEQ ID NO:5) F-aggtgaaggtgtggttccag; (SEQ ID NO:6) R-agtcattggaggtgacatcg; Pax-6 (SEQ ID NO:7) F-tctaatcgaagggccaaatg; (SEQ ID NO:8) R-tgtgagggctgtgtct-gttc; Lhx-2 (SEQ ID NO:9) F-tagcatctactgcaaggaagac; (SEQ ID NO:10) R-gtgataaaccaagtcccgag; Six-3 (SEQ ID NO:11) F-ggaatgtgatgtatgatagcc; (SEQ ID NO:12) R-tgatttcggtttgt-tctgg; Rx (SEQ ID NO:13) F-gaatctcgaaatctcagccc; (SEQ ID NO:14) R-cttcactaatttgctcaggac; C-Myb (SEQ ID NO:15) F-tacccaactgttcacgcaga; (SEQ ID NO:16) R-ctttccacaggatg-caggtt; Neurogenin-2 (SEQ ID NO:17) F-ctcttctccgaggcagt-gtt; (SEQ ID NO:18) R-ggctgccaatagtccatgtc; Hash-1 (SEQ ID NO:19) F-cggccaacaagaagatgagt; (SEQ ID NO:20) R-gc-catggagttcaagtcgtt; Crx (SEQ ID NO:21) F-atgatggcgtatat-gaaccc; (SEQ ID NO:22) R-tcttgaaccaaacctgaacc; Rhodopsin (SEQ ID NO:23) F-tcatcatggtcatcgctttc; (SEQ ID NO:24) R-catgaagatgggaccgaagt; S-Opsin (SEQ ID NO:25) F-gat-gaatccgacacatgcag; (SEQ ID NO:26) R-ctgttgcaaacaggc-caata; Recoverin (SEQ ID NO:27) F-ccagagcatctacgccaagt; (SEQ ID NO:28) R-cacgtcgtagagggagaagg; PDE-P (SEQ ID NO:29) F-aggagaccctgaacatctacc; (SEQ ID NO:30) R-at-gaagcccacttgcagc; Engrailed-1 (SEQ ID NO:31) F-ccgcac-caccaacttttcat; (SEQ ID NO:32) R-tggacagggtctctacctgc;

Math-5 (SEQ ID NO:33) F-ccgaacaggacaaactcaca; (SEQ ID NO:34) R-tcgcatcatcagacctatgg.

Figure 7:
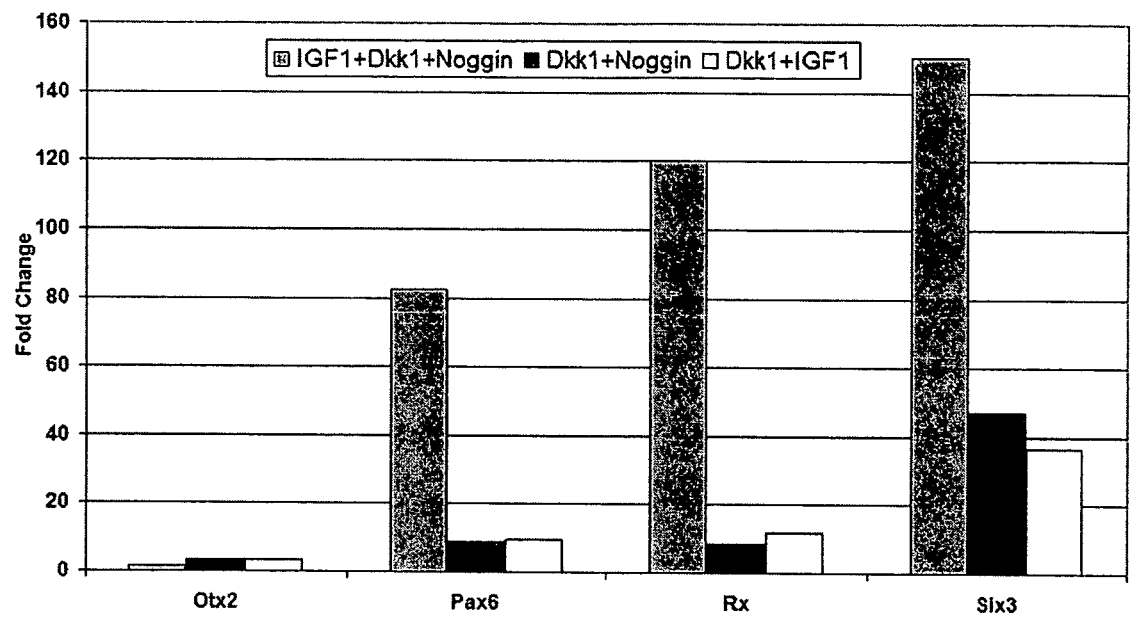

FIG. 7. Comparison of conditions.

DETAILED DESCRIPTION OF THE EMBODIMENTS

Methods are provided for the in vitro differentiation of human retinal progenitor cells from embryonic stem cells, thereby providing a scalable source of retinal progenitors and cells derived therefrom. Such cells are useful therapeutically in the treatment of visual impairment, for experimental evaluation, and as a source of lineage and cell specific products, including mRNA species useful in identifying genes specifically expressed in these cells, and as targets for the discovery of factors or molecules that can affect them.

Definitions

Retinal progenitor cells. As used herein, retinal progenitor cells are multipotent cells that can give rise to neurons, photoreceptors, and the Muller glia of the eye. The progenitor cells are generally capable of symmetric or asymmetric cell division, which may give rise to glial cells, neurons, or expansion of the progenitor cell population.

Retinal progenitor cells may be functionally characterized according to their ability to give rise to multiple lineages, or may be characterized according to the expression of genes associated with retinal development. In particular, the differentiation of retinal progenitors from embryonic stem cells is characterized by the acquisition of the expression of one or more; two or more; three or more; etc. of eye field transcription factors, which transcription factors include ET, Rx, c-myb, Crx, Pax6, Six3, Lhx2, til, Optx2, and the like. The sequences of these genes are known in the art and readily obtained. Antibodies specific for the protein products are known or may be obtained.

Retinal progenitor cells express one or more eye field transcription factors at a level at least about 10 fold increased from the expression level observed in an ES cell, and may be increased at least about 100 fold or more relative to an ES cell. In some embodiments of the invention, the one or more eye field transcription factors is Crx. In other embodiments, the one or more eye field transcription factors is Pax6. Where two or more factors are determined to be expressed, such factors may include Pax6 in combination with additional factors from the above group.

Retinal progenitor cells may also be characterized by the expression of markers for photoreceptors, e.g. opsins, PDEb, recoverin, rhodopsin, TuJ1, Hu, neurogenin2 and the like. However, expression of such markers is often at a low level in progenitor cells. The sequences of these genes are known in the art and readily obtained. Antibodies specific for the protein products are also known.

Expression of markers of interest may be detected at the mRNA or the protein level, using methods known to those of skill in the art, for example quantitative reverse PCR, taqman analysis, northern blotting, microarray hybridization, immunohistochemistry, and the like.

IGF1R agonist The IGF-1 receptor (IGF1R) is a tyrosine kinase receptor that is functionally and structurally related to the insulin receptor. The IGF1R is activated both by IGF-1 and IGF-2 but not by insulin at physiological concentrations. In some embodiments of the invention, the agonist is IGF-1. Insulin-like growth factor-1 (IGF-1) is a single-chain polypeptide of 70 amino acids. In other embodiments, the agonist is IGF-2. Alternatively, any molecule, e.g. a polypeptide molecule that binds to and activates the IGF1R receptor may be used for the purposes of the invention (see, for example, Vajdos et al. (2001) Biochemistry 40(37):11022-9). Such synthetic agonists may include antibodies and derivatives thereof, e.g. Fc fragments, single chain analogs, etc., and the like. The concentration of the agonist will be dependent on the nature of the agonist.

Where the agonist is IGF-1, the concentration will usually be at least about 0.1 ng/ml, usually at least about 0.5 ng/ml, at least about 1 ng/ml, at least about 5 ng/ml, and not more than about 1 µg/ml. Where the agonist is other than IGF-1, the concentration will provide equivalent activity to such concentrations of IGF-1.

Wnt antagonist. For the purposes of the present invention, wnt antagonists are agents that block the interaction between extracellular wnt protein and the cognate frizzled receptor on stem cells. Agents of interest may interact directly with a specific wnt, a specific set of wnts, or broadly with wnt proteins. Other agents of interest may interact directly with a specific frizzled, a specific set of frizzled proteins, or broadly with frizzled proteins. Agents of interest include blocking antibodies; or biologically active fragments thereof, e.g. Fv fragments, Fab fragments, and the like. Other antagonists of interest interact with wnt-associated proteins, e.g. Wnt co-receptors LRP5/6 and the transmembrane protein Kremen. Antagonists of interest interfere with the frizzled and/or wnt proteins that interact with stem cells. Such cells have been reported to express FZDI, FZD3, FZD4, FZD5, FZD6 (Walsh and Andrews (2003) APMIS 111(1):197-210).

A number of wnt antagonists have been described and are known in the art. Among the known wnt antagonists are members of the Dickkopf (Dkk) gene family (see Krupnik et al. (1999) Gene 238(2):301-13). Members of the human Dkk ("hDkk") gene family include Dkk-1, Dkk-2, Dkk-3, and Dkk4, and the Dkk-3 related protein Soggy (Sgy). hDkks 1-4 contain two distinct cysteine-rich domains in which the positions of 10 cysteine residues are highly conserved between family members. Exemplary sequences of human Dkk genes and proteins are publicly available, e.g. Genbank accession number NM_014419 (soggy-1); NM_014420 (DKK4); AF177394 (DKK-1); AF177395 (DKK-2); NM_015881 (DKK3); and NM_014421 (DKK2).

Other antagonists of wnt include Wise (Itasaki et al. (2003) Development 130(18):4295-30), which is a secreted protein. The Wise protein physically interacts with the Wnt co-receptor, lipoprotein receptor-related protein 6 (LRP6), and is able to compete with Wnt8 for binding to LRP6. Axin regulates Wnt signaling through down-regulation of beta-catenin (see Lyu et al. (2003) J Biol Chem. 278(15):13487-95).

Soluble forms of the ligand binding domain (CRD) of Frizzled inhibit wnt; as do the soluble frizzled related proteins (Krypta et al, J Cell Sci 2003 Jul. 1; 116(Pt 13):2627-34). The Frizzled-CRD domain has been shown to inhibit the Wnt pathway by inhibiting the binding of Wnts to the frizzled receptor (Hsieh et al. (1999) *Proc Natl Acad Sci U S A* 96:3546-51; and Cadigan et al. (1998) *Cell* 93:767-77).

The FZD8 CRD has been used as an antagonist because of its broad binding spectrum against wnt proteins; although other CRDs also find use. The CRD may be fused to another polypeptide to provide for added functionality, e.g. to increase the in vivo stability. Generally such fusion partners are a stable plasma protein that is capable of extending the in vivo plasma half-life of the CRD when present as a fusion, in particular wherein such a stable plasma protein is an immunoglobulin constant domain.

In most cases where the stable plasma protein is normally found in a multimeric form, e.g., immunoglobulins or lipoproteins, in which the same or different polypeptide chains are normally disulfide and/or noncovalently bound to form an assembled multichain polypeptide, the fusions herein containing the CRD also will be produced and employed as a multimer having substantially the same structure as the stable plasma protein precursor. These multimers will be homogeneous with respect to the CRD they comprise, or they may contain more than one CRD. Ordinarily, the CRD is fused C-terminally to the N-terminus of the constant region of immunoglobulins in place of the variable region(s) thereof, however N-terminal fusions may also find use. The transmembrane regions or lipid or phospholipid anchor recognition sequences of frizzled proteins are preferably deleted prior to fusion.

Where the antagonist is human Dkk-1, the concentration will usually be at least about 0.05 ng/ml, usually at least about 0.1 ng/ml, at least about 0.5 ng/ml, at least about 1 ng/ml, and not more than about 100 ng/ml. Where the antagonist is other than Dkk-1, the concentration will provide equivalent activity to such concentrations of Dkk-1.

BMP antagonist. For the purposes of the present invention, BMP antagonists are agents that block the interaction between extracellular certain of the BMPs and inhibit their binding to cell surface receptors. Bone morphogenetic proteins are members of the transforming growth factor beta superfamily. The activated BMP-receptor complex phosphorylates a cytosolic protein of the receptor-regulated Smad family that oligomerizes with a co-Smad and subsequently enters the nucleus to activate gene transcription of downstream targets leading to ventral fate determination. BMP antagonists act by binding to the BMP ligands and prevent the formation and activation of the BMP receptor complexes, thus promoting dorsal fate specification.

Antagonists of interest interfere with the BMP proteins that interact with stem cells. BMP-2, BMP-4 and BMP-7, inter alia, have been reported to act on embryonic stem cells (Pera et al. (2004) Journal of Cell Science 117,1269-1280).

A number of BMP antagonists have been described and are known in the art, including, for example, twisted gastrulation; chordin; noggin; Cerberus; gremlin; dan; sclerostin; etc. (Balemans and Van Hul (2002) Dev. Biol. 250,231-250).

Noggin is encoded by a single gene in mammals. Human NOG encodes a deduced 232-amino acid protein. The genetic sequence of NOG may be accessed at Genbank, accession number U31202.

Chordin belongs to a family of proteins that share a cysteine-rich pro-collagen repeat. The chordin polypeptide contains four CRs, of which the first and the third (CR1 and CR3) are responsible for BMP binding. Binding of chordin to BMP4 is specific and tight. Human CHRD encodes a 954-amino acid protein. The genetic sequence of human CHRD may be accessed at Genbank, accession number AF209928 (Millet et al. (2001) Mech. Dev. 106 (1-2), 85-96).

Twisted gastrulation (TSG) is a secreted protein with 2 conserved domains containing multiple cysteines at its amino and carboxy termini. The N-terminal domain of Tsg is sufficient to interact with BMP4 but not with chordin. Tsg competes for binding of BMP4 with the first cysteine-rich domain of chordin (CR1) but not with full-length chordin. Coexpression of Tsg with chordin leads to a more efficient inhibition of the BMP activity. The genetic sequence of human TSG may be accessed at Genbank, accession number AJ297391 (Graf et al. (2001) Mamm. Genome 124, 554-560.

Cerberus has the characteristics of both a BMP and a Wnt inhibitor. Cer1 is a secreted glycoprotein that forms dimers when expressed in mammalian cells. The human CER1 is a 267 amino acid protein. The genetic sequence of human CER1 may be accessed at Genbank, accession number AF400435.

Gremlin is an antagonist of BMP signaling that is expressed in the neural crest. It belongs to the gene family that includes Cerberus and DAN. All family members are secreted proteins that they act as BMP antagonists. The human gremlin cDNA encodes a predicted 184-amino acid protein. The genetic sequence of human gremlin may be accessed at Genbank, accession number AF110137 (Murphy et al. (1999) J. Biol. Chem. 274 (9), 5830-5834.

Sclerostin is a bone morphogenic protein (BMP) antagonist that modulates mitogenic activity through sequestering BMPs. The SOST gene encodes a deduced 213-amino acid protein, sclerostin. The protein contains a putative secretion signal and 2 N-glycosylation sites. It also contains a cystine knot motif (residues 80-167) with high similarity to the dan family of secreted glycoproteins, including dan, cerberus, gremlin), and caronte. Sost inhibits differentiation stimulated by BMP6 and BMP7, but not BMP2) and BMP4. Human SOST also antagonizes Wnt signaling by binding to the extracellular domains of the Wnt coreceptors Lrp5 and Lrp6 and disrupting Wnt-induced frizzled-Lrp complex formation. The genetic sequence of human SOST may be accessed at Genbank, accession number AF326736 (Brunkow et al. (2001) Am. J. Hum. Genet. 68 (3), 577-589).

Where the antagonist is human or mouse noggin, the concentration will usually be at least about 0.05 ng/ml, usually at least about 0.1 ng/ml, at least about 0.5 ng/ml, at least about 1 ng/ml, and not more than about 100 ng/ml. Where the ligand is other than noggin, the concentration will provide equivalent activity to such concentrations of noggin.

FGF2 activity. FGF2 is a wide-spectrum mitogenic, angiogenic, and neurotrophic factor that is expressed at low levels in many tissues. FGF2 has been implicated in a multitude of physiologic and pathologic processes, including limb development, angiogenesis, wound healing, and tumor growth. The genetic sequence of FGF2 may be accessed at Genbank, accession number M27968 (Kurokawa et al. (1987) FEBS Lett. 213 (1), 189-194).

Alternative sources of FGF2 activity are also known in the art, including molecules that are agonists of FGFR1, particularly FGFR1 IIIc isoform, where such agonists include proteins, e.g. antibodies that bind to and activate FGFR1; FGF2; FGF1; FGF19; and also including fragments; derivatives and mimetics of such factors.

Where the source of FGF2 activity (which may alternatively be referred to as an FGFR1 agonist) is human FGF2, the concentration will usually be at least about 0.05 ng/ml, usually at least about 0.1 ng/ml, at least about 0.5 ng/ml, at least about 1 ng/ml, and not more than about 100 ng/ml. Where the ligand is other than human FGF2, the concentration will provide equivalent activity to such concentrations of FGF2.

Inhibitors and growth factors useful in this invention also include derivatives, variants, and biologically active fragments of naturally occurring inhibitors, antibodies, and the like. A "variant" polypeptide means a biologically active polypeptide as defined below having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active variant will have an amino acid sequence having at least about 90% amino acid sequence identity with a native sequence polypeptide, preferably at least about 95%, more preferably at least about 99%.

Stem cells and cultures thereof. Pluripotent stem cells are cells derived from any kind of tissue (usually embryonic tissue such as fetal or pre-fetal tissue), which stem cells have the characteristic of being capable under appropriate conditions of producing progeny of different cell types that are derivatives of all of the 3 germinal layers (endoderm, mesoderm, and ectoderm). These cell types may be provided in the form of an established cell line, or they may be obtained directly from primary embryonic tissue and used immediately for differentiation. Included are cells listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)).

Stem cells of interest also include embryonic cells of various types, exemplified by human embryonic stem (hES) cells, described by Thomson et al. (1998) Science 282:1145. ES cells are considered to be undifferentiated when they have not committed to a specific differentiation lineage. Such cells display morphological characteristics that distinguish them from differentiated cells of embryo or adult origin. Undifferentiated ES cells are easily recognized by those skilled in the art, and typically appear in the two dimensions of a microscopic view in colonies of cells with high nuclear/cytoplasmic ratios and prominent nucleoli. Undifferentiated ES cells express genes that may be used as markers to detect the presence of undifferentiated cells, and whose polypeptide products may be used as markers for negative selection. For example, see US 2003/0224411 A1; Bhattacharya (2004) Blood 103(8):2956-64; and Thomson (1998), supra., each herein incorporated by reference. Human ES cell lines express cell surface markers that characterize undifferentiated nonhuman primate ES and human EC cells, including stage-specific embryonic antigen (SSEA)-3, SSEA-4, TRA-1-60, TRA-1-81, and alkaline phosphatase. The globo-series glycolipid GL7, which carries the SSEA-4 epitope, is formed by the addition of sialic acid to the globo-series glycolipid Gb5, which carries the SSEA-3 epitope. Thus, GL7 reacts with antibodies to both SSEA-3 and SSEA-4. The undifferentiated human ES cell lines did not stain for SSEA-1, but differentiated cells stained strongly for SSEA-I. Methods for proliferating hES cells in the undifferentiated form are described in WO 99/20741, WO 01/51616, and WO 03/020920.

Culture conditions of interest provide an environment permissive for differentiation, in which stem cells will proliferate, differentiate, or mature in vitro. Such conditions may also be referred to as differentiative conditions. Features of the environment include the medium in which the cells are cultured, any growth factors or differentiation-inducing factors that may be present, and a supporting structure (such as a substrate on a solid surface) if present. Differentiation is initiated by formation of embryoid bodies (EB), or similar structures.

Differentiation

ES cells or cell lines as described above can be propagated continuously in culture, using culture conditions that promote proliferation without promoting differentiation, using methods known in the art. Methods of culture are described, for example, in U.S. Patent application 20030190748 (Serum free cultivation of primate embryonic stem cells); U.S. Patent application 20040023376 (Method of making embryoid bodies from primate embryonic stem cells); U.S. Patent application 20030008392 (Primate embryonic stem cells), each herein incorporated by reference. Conventionally, ES cells are cultured on a layer of feeder cells, typically fibroblasts derived from embryonic or fetal tissue, alternatively cells can be cultured on an extracellular matrix of Matrigel™ or laminin, in medium conditioned by feeder cells or medium supplemented with growth factors such as FGF and SCF (International patent publication WO 01/51616). Under the microscope, ES cells appear with high nuclear/cytoplasmic ratios, prominent nucleoli, and compact colony formation with poorly discernable cell junctions.

Differentiation to retinal progenitors is initiated by culture of embryonic stem cells into embryoid bodies in the presence of a cocktail of factors that direct differentiation to an anterior neural fate, which cocktail includes, without limitation, an antagonist of bone morphogenetic protein (BMP) signaling pathways; an antagonist of wnt signaling pathways; and an IGF1R agonist, in the absence of basic fibroblast growth factor (FGF2) activity. Such antagonists and factors may be present as one or a combination of factors, e.g. one, two or more wnt antagonists may be used; one, two or more BMP antagonists may be used; one, two or more IGF1R agonists may be used; etc. Further, certain BMP antagonists also act as wnt antagonists, and in such cases a single protein may be added to achieve both activities.

Embryoid bodies are harvested at an appropriate stage of development, which may be determined based on the expression of markers and phenotypic characteristics of the desired cell type. The cells are cultured as embryoid bodies for at least about one day, usually at least about 2 days, more usually for around about 3 days, and for not more than about 1 week, usually for not more than 5 days.

The embryoid bodies are passaged into appropriate medium. In one embodiment of the invention, the embryoid bodies are plated on a substrate to which they can attach. Alternatively they are maintained in a suspension culture. Substrates for attachment include plates coated with gelatin or other semi-solid coating, e.g. matrigel, gelatin, agar, etc., as known in the art. The term "plates" as used herein may include Petri dishes or other tissue culture acceptable containers, e.g. 96 well plates, flasks, etc. The plating density may vary, for example from least about 1, more usually at least about 10, and not more than about $10^3$, more usually not more than about $10^2$ EB per 10 cm plate, for example at a density of about 1-2 EB/cm$^2$.

The EB are cultured under retinal differentiation (RD) conditions. Such culture conditions include a suitable medium, for example Dulbecco's minimum essential medium, and the like, and may comprise knock-out serum; serum replacement; etc. at a suitable concentration, e.g. at about 10%; and comprising B-27 supplement. The medium further comprises an antagonist of bone morphogenetic protein (BMP) signaling pathways; an antagonist of wnt signaling pathways; an IGF1R ligand; and a molecule that provides FGF2 activity, and are cultured for a period of time sufficient to allow retinal differentiation. Retinal differentiation may be accomplished in at least about 1 week; at least about 2 weeks; at least about 3 weeks; or more; and usually not more than about 6 weeks.

Following the retinal differentiation culture methods of the invention, the culture will usually comprise at least about 25% retinal progenitor cells, for example as assessed for expression of eye field transcription factors; ability to differentiate into retinal cells; and the like; more usually at least about 50% retinal progenitor cells; at least about 75% retinal progenitor cells, or more. The cells thus obtained may be used directly, or may be further isolated, e.g. in a negative selection to remove ES cells and other undifferentiated cells. Further enrichment for the desired cell type may be obtained by selection for markers characteristic of the cells, e.g. by flow cytometry, magnetic bead separation, panning, etc., as known in the art.

Markers for negative selection include markers that are selectively expressed on ES cells, fibroblasts, epithelial cells, etc. Epithelial cells may be selected for as ApCAM positive. A fibroblast specific selection agent is commercially available from Miltenyi Biotec (see Fearns and Dowdle (1992) Int. J. Cancer 50:621-627 for discussion of the antigen). Markers found on ES cells suitable for negative selection include SSEA-3, SSEA-4, TRA-I-60, TRA-1-81, and alkaline phosphatase.

Especially useful reagents are antibodies specific for markers present on the desired cells (for positive selection) and undesired cells (for negative selection). Whole antibodies may be used, or fragments, e.g. Fab, $F(ab')_2$, light or heavy chain fragments, etc. Such selection antibodies may be polyclonal or monoclonal and are generally commercially available or alternatively, readily produced by techniques known to those skilled in the art. Antibodies selected for use will have a low level of non-specific staining and will usually have an affinity of at least about 100 µM for the antigen.

For selection, separation of the subject cell population utilizes affinity separation to provide a substantially pure population. Techniques for affinity separation may include magnetic separation using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, e.g. plate, or other convenient technique. Any technique may be employed which is not unduly detrimental to the viability of the selected cells.

Specific binding members, usually antibodies, are added to the suspension of cells, and incubated for a period of time sufficient to bind the available antigens. The incubation will usually be at least about 2 minutes and usually less than about 30 minutes. It is desirable to have a sufficient concentration of antibodies in the reaction mixture so that the efficiency of the magnetic separation is not limited by lack of antibody. The appropriate concentration is determined by titration.

The suspension of cells is applied to a separation device, for example a fluorescence activated cell sorter (FACS); particle sorter, e.g. as described in U.S. Pat. No. 6,482,652; or as sold by Union Biometrica (COPAS™ systems) for large particle sorting; magnetic separation device, and the like. After the initial binding, the device may be washed with any suitable physiological buffer to remove unbound cells.

In a negative selection, the unbound cells contained in the eluate are collected as the eluate passes through the separation device. In a positive selection, the bound cells are then eluted in a suitable buffer for collection. The cells may be collected in any appropriate medium. Various media are commercially available and may be used according to the nature of the cells, including dMEM, HBSS, dPBS, RPMI, PBS-EDTA, PBS. Iscove's medium, etc., frequently supplemented with fetal calf serum, BSA, HSA, etc. Following enrichment, the percentage of cells in a population that are retinal progenitor cells may be increased to at least about 90% of the population, or more.

The methods and compositions thus obtained have a variety of uses in clinical therapy, research, development, and commercial purposes. For example, the cells find use in screening assays for factors, other agents and gene expression patterns in retinal differentiation; which may include, without limitation, assays for determining factors, other agents and gene expression patterns involved differentiation of neurons, differentiation of photoreceptors, differentiation of Muller glial cells; and the like. The cells also find use in the transplantation to restore functional neurons and photoreceptors to the eye.

Cells may be genetically altered in order to introduce genes useful in the differentiated cell, e.g. repair of a genetic defect in an individual, selectable marker, etc., or genes useful in selection against undifferentiated ES cells. Cells may also be genetically modified to enhance survival, control proliferation, and the like. Cells may be genetically altering by transfection or transduction with a suitable vector, homologous recombination, or other appropriate technique, so that they express a gene of interest. In one embodiment, cells are transfected with genes encoding a telomerase catalytic component (TERT), typically under a heterologous promoter that increases telomerase expression beyond what occurs under the endogenous promoter, (see International Patent Application WO 98/14592). In other embodiments, a selectable marker is introduced, to provide for greater purity of the desired differentiating cell. Cells may be genetically altered using vector containing supernatants over an 8-16 h period, and then exchanged into growth medium for 1-2 days. Genetically altered cells are selected using a drug selection agent such as puromycin, G418, or blasticidin, and then recultured.

The cells of this invention can also be genetically altered in order to enhance their ability to be involved in tissue regeneration, or to deliver a therapeutic gene to a site of administration. A vector is designed using the known encoding sequence for the desired gene, operatively linked to a promoter that is either pan-specific or specifically active in the differentiated cell type, e.g. photoreceptor, neuron, glial cell, etc.

Many vectors useful for transferring exogenous genes into target mammalian cells are available. The vectors may be episomal, e.g. plasmids, virus derived vectors such cytomegalovirus, adenovirus, etc., or may be integrated into the target cell genome, through homologous recombination or random integration, e.g. retrovirus derived vectors such MMLV, HIV-1, ALV, etc. For modification of stem cells, lentiviral vectors are preferred. Lentiviral vectors such as those based on HIV or FIV gag sequences can be used to transfect non-dividing cells, such as the resting phase of human stem cells (see Uchida et al. (1998) *P.N.A.S.* 95(20): 11939-44).

Combinations of retroviruses and an appropriate packaging line may also find use, where the capsid proteins will be functional for infecting the target cells. Usually, the cells and virus will be incubated for at least about 24 hours in the culture medium. The cells are then allowed to grow in the culture medium for short intervals in some applications, e.g. 24-73 hours, or for at least two weeks, and may be allowed to grow for five weeks or more, before analysis. Commonly used retroviral vectors are "defective", i.e. unable to produce viral proteins required for productive infection. Replication of the vector requires growth in the packaging cell line.

The vectors may include genes that must later be removed, e.g. using a recombinase system such as Cre/Lox, or the cells that express them destroyed, e.g. by including genes that allow selective toxicity such as herpesvirus TK, bcl-xs, etc.

Suitable inducible promoters are activated in a desired target cell type, either the transfected cell, or progeny thereof. By transcriptional activation, it is intended that transcription will be increased above basal levels in the target cell by at least about 100 fold, more usually by at least about 1000 fold. Various promoters are known that are induced in different cell types.

The cells are also useful for in vitro assays and screening to detect factors that are active on differentiating retinal cells. Of particular interest are screening assays for agents that are active on human cells. A wide variety of assays may be used for this purpose, including immunoassays for protein binding; determination of cell growth, differentiation and functional activity; production of factors; and the like.

In screening assays for biologically active agents, viruses, etc. the subject cells, usually a culture comprising the subject cells, is contacted with the agent of interest, and the effect of the agent assessed by monitoring output parameters, such as expression of markers, cell viability, and the like. The cells may be freshly isolated, cultured, genetically altered as described above, or the like. The cells may be environmentally induced variants of clonal cultures: e.g. split into independent cultures and grown under distinct conditions, for example with or without virus; in the presence or absence of other cytokines or combinations thereof. The manner in which cells respond to an agent, particularly a pharmacologic agent, including the timing of responses, is an important reflection of the physiologic state of the cell.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

In addition to complex biological agents, such as viruses, candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, New York, (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

The term samples also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1:1 to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for biological activity by adding the agent to at least one and usually a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) *Trends Biotechnol.* 17(12):477-81). Thus, antibodies can be genetically modified to provide a fluorescent dye as part of their structure. Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) *Biotechniques* 26(1):112-225; Kawamoto et al. (1999) *Genome Res* 9(12):1305-12; and Chen et al. (1998) *Genomics* 51(3):313-24, for examples.

Methods of Transplantation

The progenitor cells find use in the treatment of degenerative diseases, and may be delivered as progenitor cells; as differentiated progeny thereof, e.g. after commitment to a lineage of interest; and/or as a means of delivering gene products to the affected area. The cells are administered in a manner that permits them to graft or migrate to the intended tissue site and reconstitute or regenerate the functionally deficient area. Genetically engineered neural stem cells can be used to target gene products to sites of degeneration. These gene products can include survival-promoting factors to rescue degenerating neurons, factors that can act in an autocrine manner to promote survival and differentiation of grafted cells into site-specific neurons or to deliver neurotransmitter(s) to permit functional recovery. Ex vivo gene therapy could be used effectively as a neuroprotective strategy to prevent retinal cell loss in RP, AMD, and glaucoma and in diseases that cause retinal detachment, by the delivery of growth factors and neurotrophins such as FGF2, NGF, ciliary neurotrophic factor (CNTF), and brain derived neurotrophic factor (BDNF), which factors have been shown to significantly slow the process of cell death in models of retinal degeneration. Therapy using progenitors engineered to synthesize a growth factor or a combination of growth factors can not only ensure sustained delivery of neuroprotectants, but may also reconstruct damaged retina.

In the methods of the invention, cells to be transplanted are transferred to a recipient in any physiologically acceptable excipient comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996. Choice of the cellular excipient and any accompanying elements of the composition will be adapted in accordance with the route and device used for administration. The cells may be introduced by injection, catheter, or the like. The cells may be frozen at liquid nitrogen temperatures and stored for long periods of time, being capable of use on thawing. If frozen, the cells will usually be stored in a 10% DMSO, 50% FCS, 40% RPMI 1640 medium.

For example, cells can be introduced into the eye by intraocular injection. Intravitreal injections can be made using standard 26 G needles, where maximum volume per injection is preferably less than about 30 μl. Growth factors are optionally delivered with the cells, or following cell transplantation.

In one embodiment, cell replacement therapy is used to reverse photoreceptor degeneration in ocular diseases. Methods are known in the art for skewing the differentiation of retinal progenitor cells to photoreceptors. For example, as set forth in Kelley et al. (1995) *Development* 121, 3777-3785, herein incorporated by reference; culture of progenitor cells with 10 mM triiodothyronine enhances the differentiation of cone photoreceptors. Alternatively, sonic hedgehog has also been shown to induce photoreceptor differentiation (see Levine et al. (1997) *J. Neuroscience* 17: 6277-6288. Other factors that influence differentiation include retinoic acid (Kelley et al. (1994) *Development* 120(8):2091-102); EGF and TGF-alpha (Anchan et al. (1991) *Neuron* 6(6):923-36); dbcAMP (Taylor et al. (1990) *J Neurobiol.* 21(3):470-81); also see Kelley et al. (1995), "Regulation of proliferation and photoreceptor differentiation in fetal human retinal cell cultures", *Invest Ophthalmol Vis Sci.* 36(7):1280-9, each of which reference is specifically incorporated by reference.

Conditions of Interest for Therapy

Glaucoma is an optic nerve disorder characterized by cupping of the optic nerve head and loss of peripheral vision. Occasionally there is also loss of central vision. In the majority of patients, an elevated intraocular pressure is present and is thought to contribute to the optic nerve damage. Glaucoma is the second leading cause of blindness in developed countries (Leske, M. C. (1983) Am. J. of Epidemiology 118:166-191). Its prevalence increases with age and is greater in black patients (Leske, M. C. (1983) Am. J. of Epidemiology 118: 166-191). Glaucoma affects approximately 2.3 million Americans and blinds approximately 12,000 of them per year (Tielsch, J. M. (1993) Therapy for glaucoma: costs and consequences. In Transactions of the New Orleans Academy of Ophthalmologists, S. F. Ball, Franklin, R. M. (Ed.), pp 61-68. Kugler, Amsterdam).

The most prevalent form of glaucoma is primary open angle glaucoma (POAG), an optic neuropathy characterized by the loss of axons of the retinal ganglion cell fibers at the level of the lamina cribrosa in the optic nerve head resulting in the clinical manifestation of "cupping". In humans and non-human primates there is a normal gradient in hydrostatic pressure between inside the eye and the retrolaminar optic nerve across the optic nerve head. When intraocular pressure increases above physiological levels, the pressure gradient also increases submitting the lamina cribrosa and the retinal ganglion cell axons to deformation and mechanical stress. In glaucoma, cupping of the optic disc and compression, stretching and rearrangement of the lamina cribrosa occurs in response to elevated IOP.

Damage to the visual system in glaucoma is due to the death of the retinal ganglion cells, the axons of which comprise the optic nerve and carry the visual impulses from the eye to the brain. Thus, the ability to replace damaged nerves provides a therapeutic approach to treatment of glaucoma.

Retinitis pigmentosa (RP) refers to a heterogeneous group of hereditary eye disorders characterized by progressive vision loss due to a gradual degeneration of photoreceptors. An estimated 100,000 people in the United States have RP. Classification of this group of disorders under one rubric is based on the clinical features most commonly observed in these patients. The hallmarks of RP are night blindness and reduction of peripheral vision, narrowing of the retinal vessels, and the migration of pigment from disrupted retinal pigment epithelium into the retina, forming clumps of various sizes, often next to the retinal blood vessels.

Typically, patients first notice difficulty seeing at night due to the loss of rod photoreceptors; the remaining cone photoreceptors then become the mainstay of visual function. Over years and decades, however, the cones also degenerate, leading to a progressive loss of vision. In most RP patients, visual field defects begin in the midperiphery, between 30° and 50° from fixation. The defective regions gradually enlarge, leaving islands of vision in the periphery and a constricted central field (called tunnel vision). When the visual field contracts to 20° or less and/or central vision is 20/200 or worse, the patient becomes legally blind.

Inheritance patterns indicate that RP can be transmitted in X-linked (XLRP), autosomal dominant (ADRP), or recessive (ARRP) modes. Among the three genetic types of RP, ADRP is the mildest. These patients often retain good central vision to 60 years of age and beyond. In contrast, patients with the XLRP form of the disease are usually legally blind by 30 to 40 years of age. However, the severity and the age of onset of the symptoms varies greatly among patients with the same genetic type of RP. This variation is apparent even within the same family when presumably all the affected members have the same genetic mutation. Many RP-inducing mutations have now been described. Of the genes identified so far, many encode photoreceptor-specific proteins, several being associated with phototransduction in the rods, such as rhodopsin, subunits of the cGMP phosphodiesterase, and the cGMP-gated $Ca^{2+}$ channel. Multiple mutations in each of the cloned genes have been found. For example, in the case of the rhodopsin gene, 90 different mutations have been identified among ADRP patients.

Regardless of the specific mutation, the vision loss that is most critical to RP patients is due to the gradual degeneration of cones. In many cases, the protein that the RP-causing mutation affects is not even expressed in the cones; the prime example is rhodopsin-the rod-specific visual pigment. Therefore, the loss of cones may be an indirect consequence of a rod-specific mutation. The ability to replace damaged photoreceptors provides an approach to the treatment of this disease.

Age-related macular degeneration (AMD) causes a progressive loss of central vision, and is the most common cause of vision loss in people over age 55. The underlying pathology is degeneration of the photoreceptors. Various studies have implicated hereditary factors, cardiovascular disease, environmental factors such as smoking and light exposure, and nutritional causes as contributing to the risk of developing AMD. RPE degeneration is accompanied by variable loss of both the overlying photoreceptors and the underlying choroidal perfusion. Visual acuity loss or visual field loss occurs when the RPE atrophies and results in secondary loss of the overlying photoreceptor cells that it supplies. The ability to replace RPE and photoreceptor cells provides a means of treating established AMD.

Macular degeneration is broadly divided into two types. In the exudative-neovascular form, or "wet" AMD, which accounts for 10% of all cases, abnormal blood vessel growth occurs under the macula. There is formation of a subretinal network of choroidal neovascularization often associated with intraretinal hemorrhage, subretinal fluid, pigment epithelial detachment, and hyperpigmentation. Eventually, this complex contracts and leaves a distinct elevated scar at the posterior pole. These blood vessels leak fluid and blood into the retina and thus cause damage to the photoreceptors. Wet AMD tends to progress rapidly and can cause severe damage; rapid loss of central vision may occur over just a few months.

The remaining 90% of AMD cases are atrophic macular degeneration (dry form), where there is pigmentary disturbance in the macular region but no elevated macular scar and no hemorrhage or exudation in the region of the macula. In these patients there is a gradual disappearance of the retinal pigment epithelium (RPE), resulting in circumscribed areas of atrophy. Since photoreceptor loss follows the disappearance of RPE, the affected retinal areas have little or no visual function. Vision loss from dry AMD occurs more gradually over the course of many years. These patients usually retain some central vision, although the loss can be severe enough to compromise performance of tasks that require seeing details.

When the appropriate age and clinical findings are accompanied by the loss of visual acuity, visual field, or other visual functions, the condition often is classified as AMD. At times, the step prior to the onset of visual loss has been classified as AMD if the patient has characteristic drusen and relevant family history.

Occasionally, macular degeneration occurs at a much earlier age. Many of these cases are caused by genetic mutations. There are many forms of hereditary macular degeneration, each with its own clinical manifestations and genetic cause.

The most common form of juvenile macular degeneration is known as Stargardt disease, which is inherited as an autosomal recessive. Patients are usually diagnosed under the age of 20. Although the progression of vision loss is variable, most of these patients are legally blind by age 50. Mutations that cause Stargardt disease have been identified in the ABCR gene, which codes for a protein that transports retinoids across the photoreceptor membrane.

Kits

The formulations of the invention are optionally packaged in a suitable container with written instructions for a desired purpose. Such formulations may comprise a cocktail of retinal differentiation factors, in a form suitable for combining with cells. Such a composition may further comprise suitable buffers and/or excipients appropriate for transfer into an animal. Such compositions may further comprise cells to be engrafted.

For further elaboration of general techniques useful in the practice of this invention, the practitioner can refer to standard textbooks and reviews in cell biology, tissue culture, embryology, and cardiophysiology. With respect to tissue culture and embryonic stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998).

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXAMPLES

Methods are shown to be developed for deriving retinal neurons from human embryonic stem cells (hES). To direct the ES cells to an anterior neural fate, we treated embryoid bodies with a combination of noggin (a potent endogenous inhibitor of the BMP pathway) and Dickkopf-1 (dkk1; a secreted antagonist of the Wnt1beta-catenin signaling pathway) and IGF-1. The embryoid bodies were cultured for 3 days in the three factors (FIG. 1a-d) and then transferred to 6 well plates coated with either Matrigel or laminin where they were allowed to attach. The cells were then maintained in the same medium, with bFGF added, for an additional three weeks; we refer to this protocol as retinal determination (RD) conditions.

Figure 1:
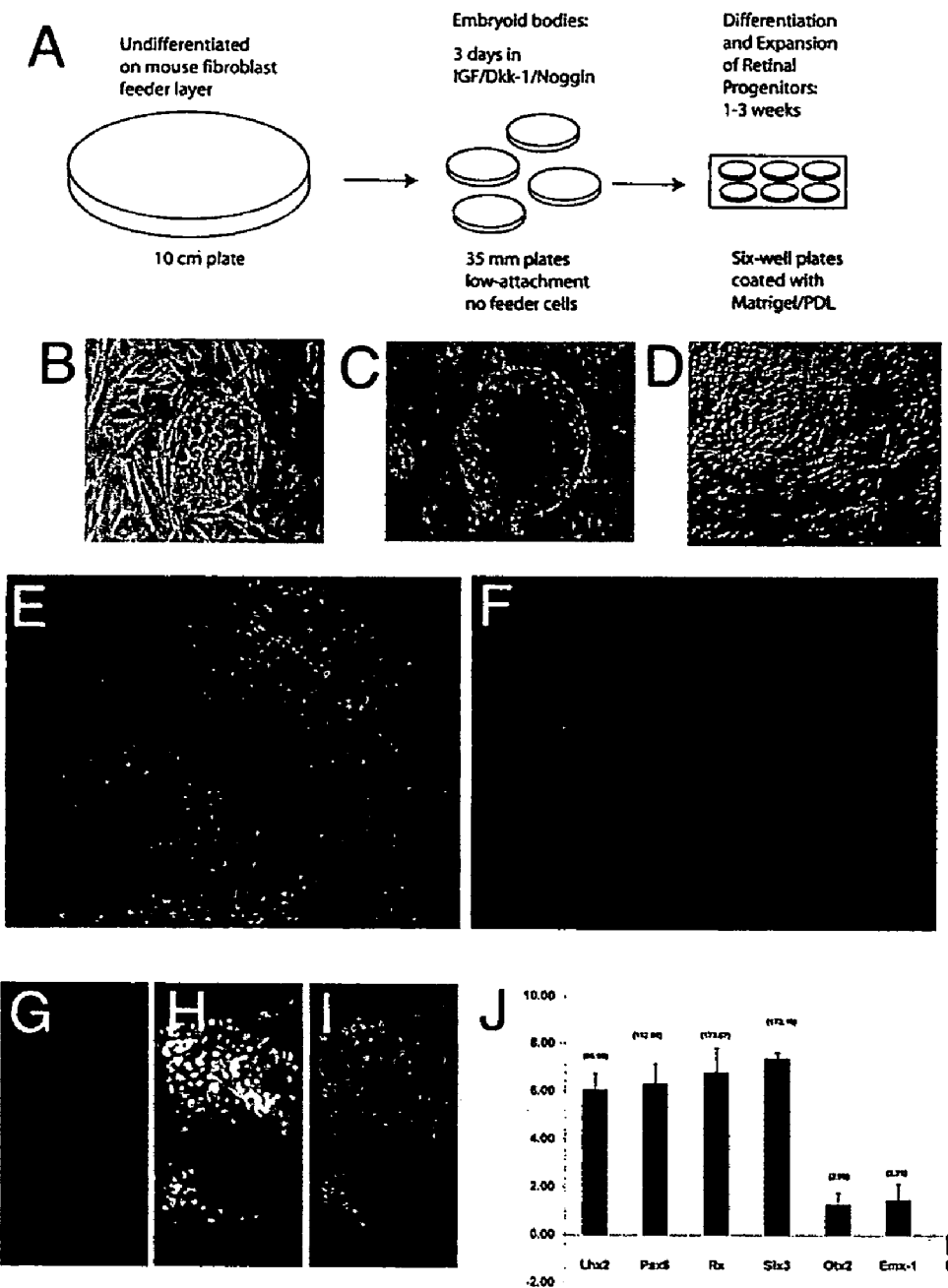
FIG. 1. Efficient Retinal Induction of hES cells. 1a shows a schematic of the 3-week retinal determination protocol. 1b-d show brightfield phase images of the progression of undifferentiated hES cells (b) though embryoid body (c) to formation of neural rosettes (d). At the end of three weeks approximately 80% cells show immunoreactivity to retinal progenitor markers like Pax6 (e) and Chx10 (f). 1g-i shows co-labeling by a number of cells for Sox2 (g) and Pax6 (i) antigen. QPCR analysis of EFTFs at the end of 1 week under retinal determination conditions (n=3; mean+S.E.M.) shows a 6-8 cycle (approximately 80- 170 fold) increase in various retinal stem cell markers (Pax6, Lhx2, Rx and Six3) with no significant increase in genes expressed elsewhere in the CNS (En-1, Emx-1 and Otx2)

The presumptive eye field is defined by a group of transcription factors expressed in this region (eye field transcription factors; EFTFs), including ET, Rx, Pax6, Six3, Lhx2, tll and Optx2/Six6. After the ES cells had been exposed to the RD conditions for one, two or three weeks, we harvested the mRNA and analyzed the levels of expression for the EFTFs. FIG. 1j shows the relative expression levels for cells after one week in RD conditions. We found a 6-8 cycle (85-175 fold) increase in the expression of the EFTFs, including Rx, Pax6, Lhx2, and Six3 (FIG. 1j) over the levels in the undifferentiated cells. By contrast, genes expressed in other regions of the CNS, like the cerebral cortex (Emx-1) or hindbrain (Engrailed-1) show no significant increase over the undifferentiated ES cells. We also characterized the hES cells with immunofluorescence for retinal progenitor markers. FIG. 1e-i shows the extensive labeling for Pax6, Chx10 and Sox2. Quantitative analysis of the cultures showed that 78% of the cells were labeled with Pax6 antibodies at the end of 3 weeks in RD conditions. Most of the Pax6 labeled cells were also labeled with antibodies to Sox2 (FIG. 1g-i).

Figure 2:
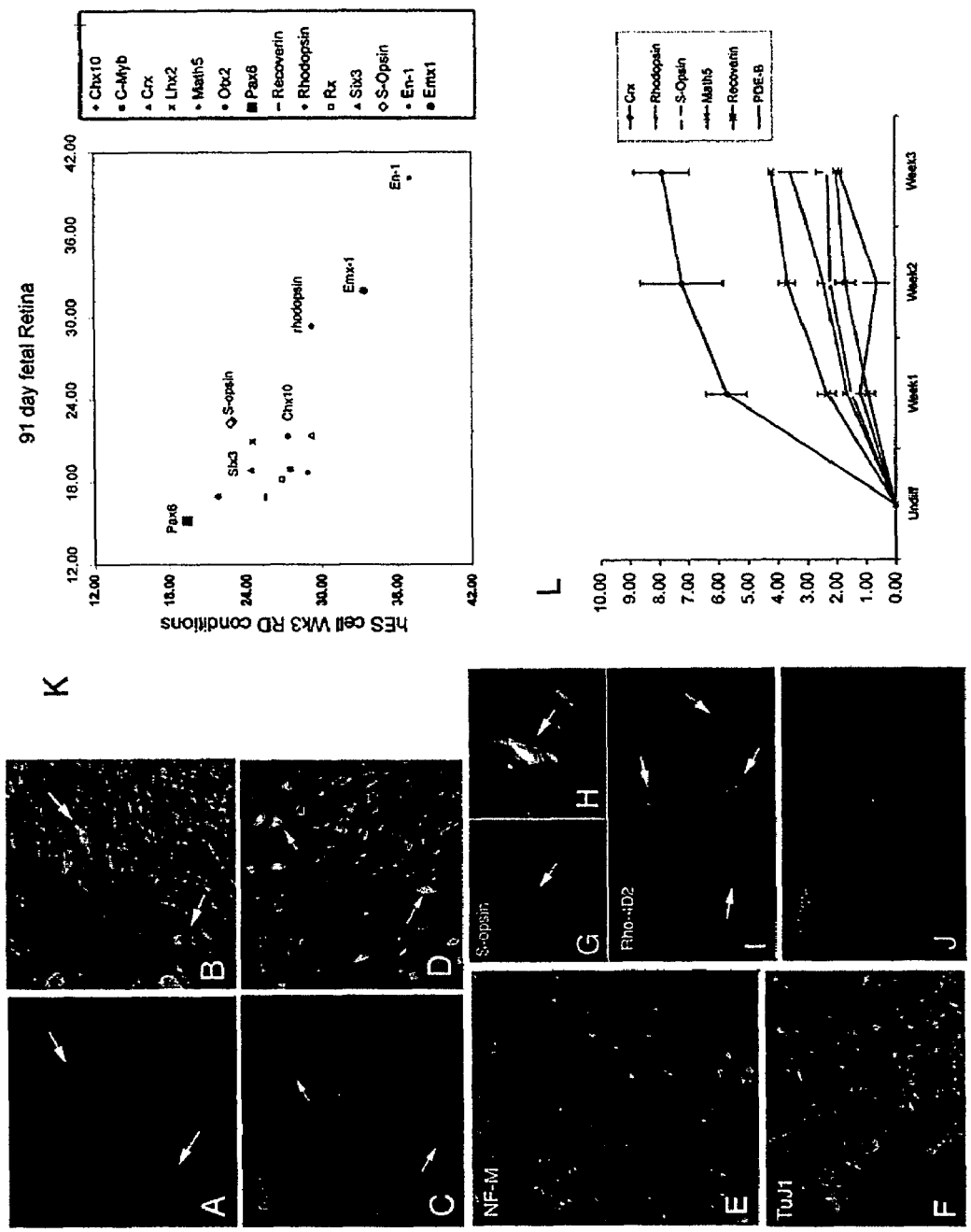
FIG. 2. Multi-lineage differentiation of hES cell-derived retinal progenitors. 2a shows two levels of Pax6 expression in these cells. Progenitors express lower levels of Pax6, while differentiating ganglion and amacrine cells express high levels of Pax6 and coexpress Hu C/D (2b, green). 2c,d show similar pattern of Pax6 and Hu C/D expression in dissociated 78 day human fetal retinal cultures for comparison. Human ES cells in RD conditions label for neurofilament-M (e) and Tuj-1 (f). (2g,h). A cell expressing S-opsin in UV and Nomarski optics, respectively. 2i cells labeled with the rod photoreceptor marker Rho-4D2 (rhodopsin). (2j) Many cells express the rod photoreceptor specific transcription factor, Nrl (red); nuclei are also labeled with DAPI (blue). (2k) Comparative QPCR analysis of expression of various genes between a 91 day human fetal retina and hES cells after 3 weeks under RD conditions, showing the correlation between hES cell derived retinal cells and retinal cells isolated from fetal human retina. (2L) QPCR analysis of retinal differentiation genes (n=3). The graph shows a steady increase in retinal neuronal markers Crx, Math5, S-opsin, rhodopsin/recoverin and PDE-β over the duration of three weeks of induction.

These data demonstrate that a large fraction of the hES cells in cultures kept under RD conditions develop characteristics of retinal progenitors. To determine whether the hES cell derived progenitors have the capacity for multi-lineage differentiation characteristic of retinal progenitors, we used immunofluorescence for specific types of retinal neurons, including hu C/D, neurofilament-M, and tuj-1 for ganglion and amacrine cells, Crx, Nrl, recoverin, S-opsin, and rhodopsin for photoreceptors, and Prox1 for amacrine and horizontal cells. All of these markers have been previously described in retinal neurons of various species. As noted above, most cells in the cultures express Pax6; however, some cells showed a distinct increase in the Pax6 level, characteristic of ganglion cells and amacrine cells (FIG. 2a). The cells that express a high level of Pax6 are also labeled with antibodies against Hu, another protein expressed by amacrine and ganglion cells (FIG. 2b). Primary cell cultures derived from a 78 day human fetal retina show a very similar pattern of labeling with Pax6 and Hu (FIG. 2c,d), as do sections from the developing human retina. Many cells in the hES cultures also label with other markers of ganglion and amacrine cells: tuj-1 and neurofilament-M (FIG. 2e,f), while other cells are labeled with photoreceptor-specific antibodies, including S-opsin, rhodopsin and Nrl (FIG. 2g-j). In addition to the antibody labeling, we analyzed the cultures for expression of genes associated with retinal photoreceptors by QPCR. FIG. 2l shows the results of this analysis. There is a large and stable increase in the level of Crx (the earliest known photoreceptor marker) in the cells, as early as one week in RD conditions. While the other photoreceptor differentiation markers, like the opsins, PDE-β and recoverin, show only modest increases at one week, they steadily increase over the time in vitro (FIG. 2l). This is consistent with the developmental timing of expression of these genes in the retina: first Crx, then recoverin and PDE-β and lastly the opsin genes.

To more precisely determine the degree to which the ES cell derived retinal progenitors resemble those from the developing retina, we collected mRNA from the retinas of a human fetus at 91 days post-conception, an age when there are both progenitors, and newly differentiating neurons. When we compare EFTF expression and the expression of genes specific to differentiating neurons, between the fetal retina and ES cells kept under RD conditions for three weeks, we find an excellent correlation (FIG. 2k). The degree of expression of the EFTFs is similar in the ES cell-derived retinal progenitors and those obtained from the fetal retina. However, although all of the photoreceptor markers are expressed in both groups of cells, their expression is somewhat reduced in the ES cell derived progenitors, as compared to the fetal-derived cells, suggesting that the RD conditions promote the expansion of the progenitor pool relative to the differentiating neurons and photoreceptors. These results show that hES cells, under RD conditions, develop into a mix of progenitors and retinal neurons and photoreceptors cells that bear a striking resemblance to human fetal retinal cultures.

Figure 3:
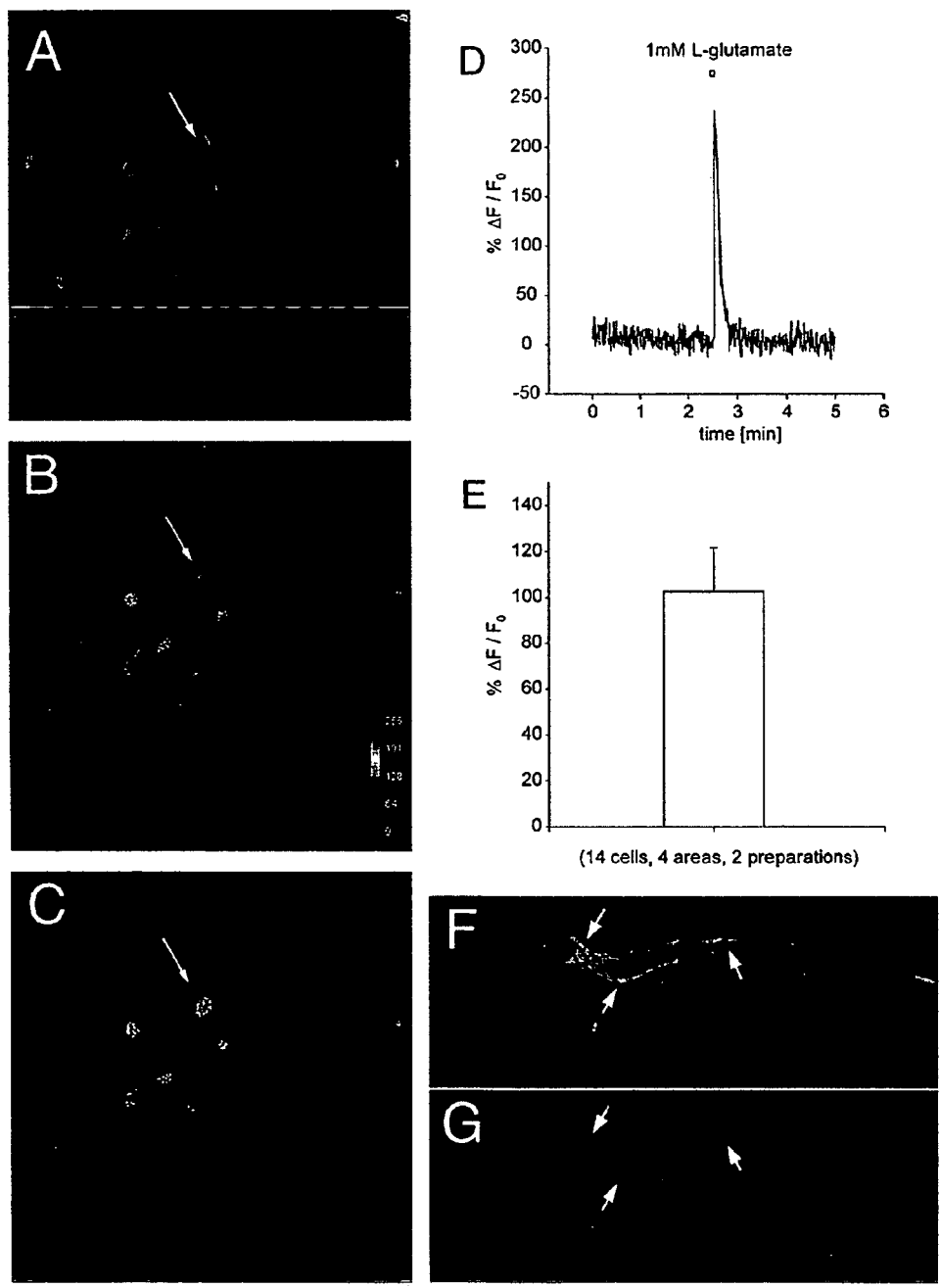
FIG. 3. Glutamate induced calcium changes in hES cell-derived retinal neurons. 3a shows Oregon Green BAPTA-1 AM loading of the hES derived neurons. 3b shows the same cells at baseline using a rainbow LUT pallete. In 3b, the same field of cells is shown immediately following application of 1 mM glutamate. Arrow in a,b,c indicates a cell with large calcium transient following application. 3d shows the calcium change in the same cell expressed as a pseudo-ratio of fluorescence change expressed as a % $\delta F/F_0$ over time. 2e shows pooled fluorescence change from 14 randomly selected cells from 4 preparations. 2f,g. Cells with neuronal morphology and expressing internexin (green) show punctuate labeling with synaptophysin (red) antibody, a protein expressed in synapses.

To analyze the functional maturation of the retinal neurons produced in these cultures, we re-dissociated the cells and plated them at lower density. This allowed us to analyze small clusters of cells with calcium imaging techniques. We found that some of the cells, particularly those with distinct neuron-like morphology, respond to glutamate with substantial calcium fluxes (FIG. 3a-e). Since most inner retinal neurons have glutamate receptors, these data lend further support to the immunofluorescent identification of ganglion cells and amacrine cells. In addition to functional glutamate receptors, cells with neuronal morphology displayed synaptophysin labeled puncta, consistent with synaptic development in vitro (FIG. 3f,g).

Figure 4:
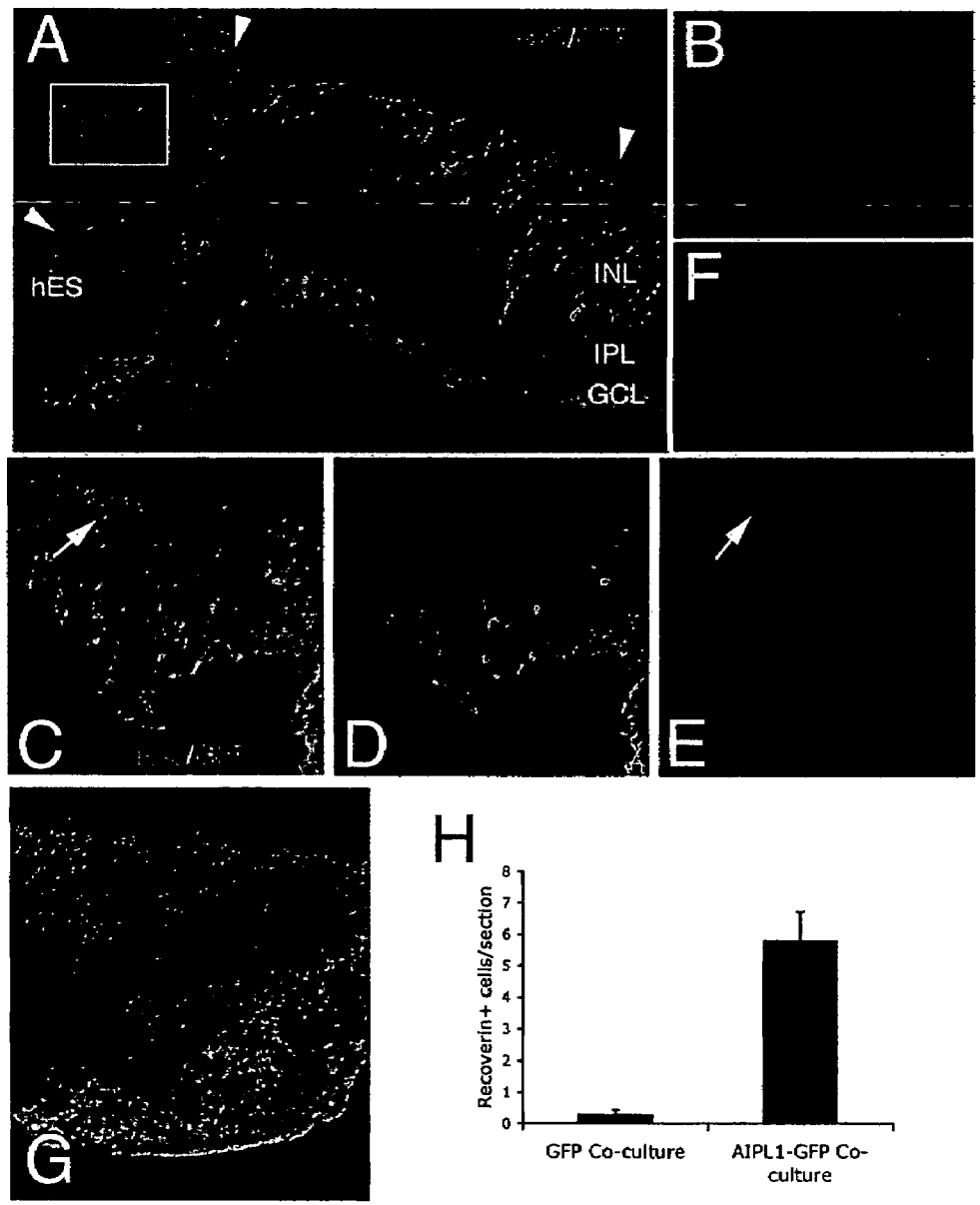
FIG. 4. Explant co-culture of hES-derived retinal progenitors with retinas of Aipl1 -/- GFP mice. 4a shows the mouse retina in green (GFP) with the outer nuclear layer missing (degenerated). Many of the hES cells express Pax6. 4b shows an enlarged view of boxed area in 4a. 4c-f shows recoverin expression, a marker of photoreceptors, in the co-cultures. 4c shows a merged view of 4d&e where 4d is showing mouse cells expressing GFP and in 4e is recoverin expression in a number of hES cell-derived neurons. Some mouse bipolars show recoverin and GFP co-expression. 4f is a higher magnification of the region identified by the arrow in 4c-e showing recoverin expressing hES cell-derived retinal neurons. 4g confirms the identity of the recoverin (red) expressing cells in hES region using co-labeling with human specific nuclear marker (blue). 4h. Graph showing number of recoverin expressing hES cell-derived neurons per section (n=3; mean+ S.E.M.) from co-cultures with wild-type mice expressing GFP and Aipl1-/- GFP mice.
Figure 5:
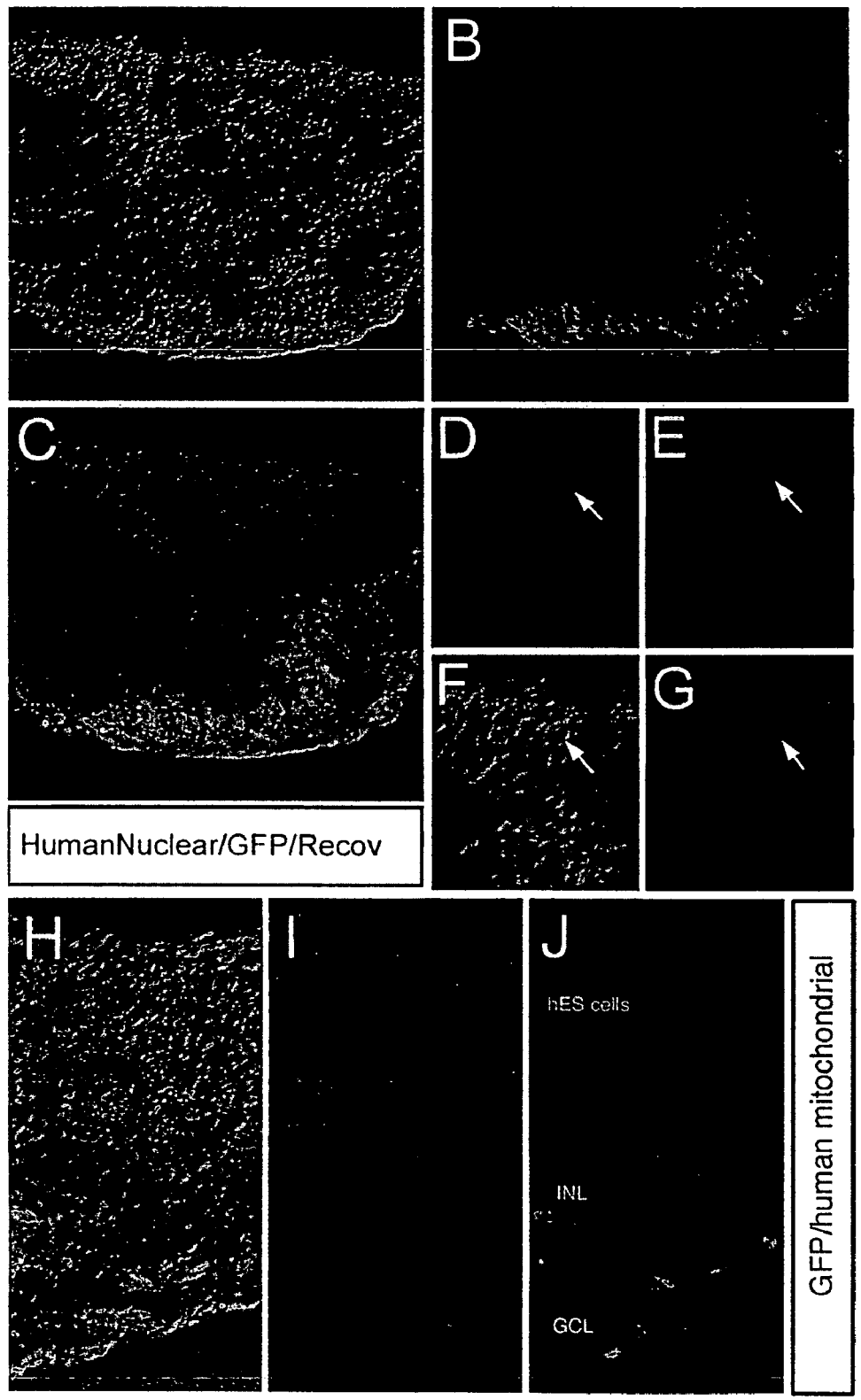
FIG. 5. Explant co-culture experiments with Aipl1 -/- GFP mice. The figure shows a brightfield image using Nomarski optics (A) alongside staining with GFP for mouse tissue and human specific nuclear marker for hES cell-derived retinal progenitors (B) as well as human specific mitochondrial marker (H-J). In the middle (CG) is a representative section triple-stained for GFP (green), human nuclear marker (blue) and recoverin (red) showing that the recoverin expressing cells co-label with human nuclear marker.

Although the majority of well differentiated neurons in the cultures display characteristics of amacrine and ganglion cells, many cells also express markers for immature photoreceptors, including Crx, and Nrl. However, only a very few cells express markers of more differentiated photoreceptors. To stimulate photoreceptor differentiation from the hES cells, we cocultured the hES cell-derived progenitors with retinal explants from adult mice on 0.4 um filters. The co-cultures were allowed to survive up to 6 days, and analyzed for evidence of hES cell differentiation and integration into the mouse retina. The mice had GFP stably expressed in all cells (via the chicken β-actin promoter/CMV enhancer) and are easily distinguished from the human cells. In addition, we labeled the human cells with one of two different human-specific antibodies: a human nuclear antibody and a human mitochondrial antibody (FIG. 4f and FIG. 5). The retinal progenitors derived from hES cells integrated with the mouse retina, and most express Pax6 (FIG. 4a,b). We co-cultured the hES cells with both wild type mouse retinas and with retinas from mice with a mutation that causes photoreceptor degeneration (Aipl1 −/−). In the co-cultures with the Aipl1 −/− retinas, recoverin immunoreactive cells, that resemble photoreceptors, are observed (FIG. 4c-g); interestingly, recoverin immunoreactive cells are rarely found when hES cells are co-cultured with wild type mouse retina (FIG. 4h). Other photoreceptor markers, Crx and Nrl, were also expressed by more of the hES cell-derived retinal progenitors that were co-cultured, than when these cells were cultured without mouse retinas.

To test the importance of the factors present in the medium, an experiment was performed as described above, except that either IGF-1 or Noggin was omitted from the media. bFGF was added in each case on the 4th day. At the end of 1 week, gene expression for the eye field transcription factors was compared in each of the three cases (IGF1+Dkk1+Noggin, Dkk1+noggin and IGF1+Dkk1). The data show that the combined cocktail of factors had a significant increase in retinal progenitor cells when compared to the use of only two of the factors.

Our data demonstrate that human ES cells can be directed to a retinal progenitor identity with high efficiency by using a combination of noggin, dkk1 and IGF-1. A key difference between human and mouse ES cells appears to be their different response to noggin. The addition of IGF-1 to the embryoid bodies specifically and efficiently directs the cells to a retinal progenitor identity, as evidenced by the fact that we found only very low levels of expression of genes associated with cerebral cortex or midbrain in our cultures. One of the most striking features of these cultures is that they are accelerated in "developmental time" over normal human embryological development. Less than two weeks after an undifferentiated state, the cells have acquired the characteristics of the eye field, and specifically the neural retina part of the optic cup. The optic vesicle does not become distinct in the human embryo until Streeter's horizon 11 or 12, or approximately postovulatory day 24-26. The development of an inner "neuroblastic layer" and optic fibers, indicative of the onset of retinal ganglion cell genesis, does not occur until approximately the $6_{th}$ postovulatory week. Consistent with this is the fact that the gene expression profile of the hES cells after 3 weeks in RD conditions resembles that of the 91 day (postconception) fetal retina (albeit with a reduced expression of photoreceptor genes). The hES cells are therefore accelerated by 3-4 weeks over the normal human developmental time course.

The degeneration of neurons and photoreceptors in the retina that occur in a number of disorders are common causes of blindness for which there are currently few therapies. The repair of the retina with replacement cells derived from human ES cells provides the basis for new approaches for treating a wide variety of retinal degenerations. In this study, we report a method for directing pluripotent hES cells to a retinal progenitor identity. The hES-derived retinal progenitors are virtually indistinguishable from retinal progenitors derived from human fetal stages, using both RT-PCR and immunofluorescence labeling. The retinal progenitor cells are able to integrate with retinas from a mouse model of Leber's Congenital Amaurosis caused by a mutation in the Aipl-1 gene that causes photoreceptor degeneration, and new photoreceptors differentiate from the hES cells in these co-cultures. Thus, hES cells may provide an excellent source of new neurons and photoreceptors for retinal repair.

Materials and Methods

Cell Culture and Retinal Induction: The H-1 (WA-01) human embryonic stem cell line was obtained from Wicell Research Institute. The cells were cultured and passaged on a feeder layer made of irradiated mouse embryonic fibroblasts. Embryoid bodies were formed by treating undifferentiated hES colonies with 1 mg/ml of type IV collagenase (Invitrogen) and resuspending them in a 6 well ultra-low attachment plate (VWR) in the presence of media containing DMEM:F12 (Gibco), 10% knockout serum (Invitrogen), B-27 supplement (Invitrogen), 1 ng/ml mouse noggin (R&D Systems), 1 ng/ml human recombinant Dkk-1 (R&D Systems) and 5ng/ml human recombinant insulin-like growth factor-1 (IGF-1) (R&D Systems). The cells were cultured as embryoid bodies for 3 days. On the fourth day, the embryoid bodies were plated onto poly-D-lysine-Matrigel (Collaborative Research, Inc) coated plates and cultured in the presence of DMEM:F12, B-27 supplement, N-2 Supplement (Invitrogen), 10 ng/ml mouse noggin, 10 ng/ml human recombinant Dkk-1, 10 ng/ml human recombinant IGF-1 and 5ng/ml human recombinant basic fibroblast growth factor (bFGF) (R&D Systems). The media was changed every 2-3 days.

Immunocytochemistry and Immunohistochemistry: Cells and eyes were fixed with 4% paraformaldehyde and analyzed with the following antibodies: rabbit anti-recoverin, mouse anti-Tuj-1 (Covance), mouse anti-Hu C/D (Molecular Probes), rabbit anti-neurofilament-M (Chemicon), mouse anti-NCAM (DHSB), mouse anti-Rho-4D2, mouse anti-Pax6 (DHSB), rabbit anti-Pax6 (CRP), mouse anti-human nuclear antigen (Chemicon), mouse anti-human mitochondrial antigen (Chemicon), rabbit anti-GFP, mouse anti-GFP (Molecular Probes), goat anti-Sox2 (Santa Cruz), rabbit anti-Chx10, rabbit anti-Prox1 (Chemicon), rabbit anti-S-opsin, rabbit anti-Nrl, rabbit anti-Crx, rabbit anti-internexin (Chemicon) and mouse antisynaptophysin (Chemicon). Secondary antibody staining was done using the corresponding Alexa-488, Alexa-568 and Alexa-350 fluorescent-tagged antibodies (Molecular Probes).

Real time quantitative PCR analysis. Total RNA was extracted from the cultures using TriZol (Invitrogen) followed, by chloroform extraction as per manufacturer's instructions. This was followed by DNAse-1 (Qiagen) treatment followed by RNA cleanup using Qiagen RNA mini cleanup kit. cDNA was reverse transcribed using Superscript II RT kit (Invitrogen) as per manufacturer's instructions. Q-PCR was performed for various genes (FIG. 6) and results normalized to β-actin levels.

Animals: All experiments were done in accordance with approved protocols and the animals were housed and bred in the Department of Comparative Medicine at the University of Washington. Wild type albino, as well as Aipl1−/− mice (Ramamurthy et al., 2004) bred onto a global GFP expressing background (Jackson Labs) were used for in vitro explant co-culture experiments.

In Vitro Explant Co-Culture Experiments: Whole retinas were cultured on a nitrocellulose membrane for up to two weeks in vitro, in a method modified from Caffe et al., 1989. Briefly, retinas from mice were dissected free from the lens, pigmented epithelium and extra-ocular tissue in Hanks's balanced salt solution (HBSS), four small incisions were made in the peripheral retina to allow better flattening, and retinas were placed photoreceptor side down on a Millicell-CM 0.4 μm filter insert. Filters were placed into a 6-well plate containing 1 mL of explant media (DMEM:F12 (Gibco), 0.6% glucose, 5 nM Hepes, 0.11% NaHCO3, 25 μg/mL insulin, 100 μg/mL transferrin, 60 μM putrescine, 30 nM selenium, 20 nM progesterone, 800 nM L-Glutamine, penicillin and streptomycin (Gibco), N2 supplement, and 10% FBS (Gibco)). Explants were cultured at the gas-liquid interface at 37° C., 5% $CO_2$ and media was replaced every other day. The day following placement of explants onto the nitrocellulose membrane, a suspension of hES cells was gently dropped onto the surface of the explant. The explants were maintained for 6 days on the nitrocellulose membrane. For immunohistochemical analysis, the explants were fixed with 4% PFA and gently lifted off the membrane. They were subsequently embedded in OCT and cryosectioned.

Calcium Imaging of glutamate responses Intracellular calcium $[Ca_{2+}]_i$ transients in hES cells after >3 weeks in RD conditions were studied. Cells were kept serum-free for an hour and then loaded with 8 μM acetomethoxy (AM) ester form of Oregon green®488 BAPTA-1 (Molecular Probes, Eugene, USA) in bath solution (see below) with 0.05 mg/ml pluronic acid for 30 min at 37° C. (95% $O_2$, 5% $CO_2$). Cells were transferred to a recording chamber (1 ml volume) and perfusated with bath solution (adapted from the cell culture media containing in mM: 119 NaCl, 4.16 KCl, 2.5 $CaCl_2$, 0.3 $MgCl_2$, 0.4 $MgSO_4$, 0.5 $Na_2HPO_4$, 0.45 $NaH_2PO_4$, 20 Hepes, 19 glucose) at rate of 1 ml/min at 35-37° C. and pH of 7.4. Fluorescence was monitored using a laser-scanning confocal microscope (Zeiss LSM5/Axioskop2 MOT, Jena, Germany). Fluorescence images (excitation at 488 nm; emission >505 nm; maximal pinhole opening) were acquired at 2 Hz and 387 ms exposure time per image at a resolution of 256×256 pixels. Images were processed and analyzed using ImageJ software. The fluorescence changes (%$\Delta F/F_0$) for individual cells were calculated using the formula % $\Delta F/F_0=(F_1-F_0)*100/F_0$, where $F_1$ was the fluorescence averaged over the pixel of a cell soma following a stimulus, while $F_0$ was the average fluorescence of that cell prior to stimulus application, averaged over three images. Background intensity was zero. Before drug application, cells were perfusated for over 10 min. For stimulation experiments, a glass electrode was filled with either bath solution (control) or bath solution containing 1 mM glutamate. The electrode was connected to a PicoSpritzer (PLI-100, Medical Systems Corp., Greenvale, USA), which delivered 100 ms air puffs which propelled 10 μl solution over the area of interest during continuous perfusion. All data presented were analyzed using Student's t-test.

Human Fetal Eyes Eyes from 78-95 days post-conception fetuses, without identifiers, were obtained from therapeutic abortions through fetal tissue bank at the University of Washington. Individual eyes were rinsed with sterile HBSS; retinas were then dissected from other ocular tissue. The retinas were then either cultured on Matrigel-coated coverslips or fixed in 4% paraformaldehyde for subsequent freezing in OCT or used for RNA extraction using TriZol.

The compositions and procedures provided in the description can be effectively modified by those skilled in the art without departing from the spirit of the invention embodied in the claims that follow.

The invention claimed is:

1. A method for in vitro differentiation of human retinal progenitor cells from human embryonic stem cells, the method comprising:
   culturing said human embryonic stem cells to embryoid bodies in a conditioning medium comprising at least 1 ng/ml of insulin-like growth factor 1 (IGF-1), at least 1 ng/ml Dkk-1 and at least 1 ng/ml Noggin for 1 to 7 days in the absence of basic fibroblast growth factor (FGF2) activity; then
   culturing the resulting embryoid bodies in retinal differentiation medium comprising at least 1 ng/ml of insulin-like growth factor 1 (IGF-1), at least 1 ng/ml Dkk-1, at least 1 ng/ml Noggin and at least 5 ng/ml FGF-2 for at least one week,
   thereby yielding human retinal progenitor cells.

2. The method according to claim 1, wherein said embryoid bodies are plated to adhere to a semi-solid substrate prior to culturing in retinal differentiation medium.

3. The method according to claim 2, wherein said semi-solid substrate comprises matrigel extracellular matrix protein.

4. The method according to claim 1, the method further comprises quantitating retinal progenitor cells in said culture.

5. The method according to claim 4, wherein said quantitating comprises determining the expression of eye field transcription factors by cells yielded by said culturing in said retinal differentiation medium.

6. The method according to claim 5, wherein said determining is performed by quantitative PCR.

7. The method according to claim 5, wherein said determining is performed by antibody binding.

8. The method according to claim 1, wherein following said culturing step, the cells are further selected to enrich for retinal progenitor cells.

* * * * *

UNITED STATES PATENT AND TRADEMARK OFFICE
CERTIFICATE OF CORRECTION

PATENT NO. : 7,541,186 B2 Page 1 of 1
APPLICATION NO. : 11/361051
DATED : June 2, 2009
INVENTOR(S) : Thomas Reh It is certified that error appears in the above-identified patent and that said Letters Patent is hereby corrected as shown below:

• Column 1, line 10: please delete "may have" and insert --has--, so that the sentence reads as follows:

The government has certain rights in this invention.

• Column 34, line 29: please delete "matrigel", so Claim 3 reads as follows:

3. The method according to claim 2, wherein said semi-solid substrate comprises extracellular matrix protein.

Signed and Sealed this

Twentieth Day of October, 2009

David J. Kappos
*Director of the United States Patent and Trademark Office*